United States Patent [19]

Cannata et al.

[11] Patent Number: 4,557,866
[45] Date of Patent: Dec. 10, 1985

[54] PROCESS FOR THE SYNTHESIS OF PYRIDO-IMIDAZO RIFAMYCINS

[75] Inventors: Vincenzo Cannata, Borgo Nuovo di Pontecchio Marconi; Gian F. Tamagnone, Casalecchio di Reno, both of Italy

[73] Assignee: ALFA Farmaceutici S.p.a., Bologna, Italy

[21] Appl. No.: 727,521

[22] Filed: Apr. 26, 1985

[30] Foreign Application Priority Data

May 15, 1984 [IT] Italy .................... 3463 A/84

[51] Int. Cl.[4] .................... C07D 491/22
[52] U.S. Cl. .................... 260/239.3 P
[58] Field of Search .................... 260/239.3 P

[56] References Cited
U.S. PATENT DOCUMENTS 4,341,785 7/1982 Marchi et al. .................... 260/239.3 P Primary Examiner—Robert T. Bond
Attorney, Agent, or Firm—Bucknam and Archer

[57] ABSTRACT

A new process for the synthesis of pyrido-imidazo-rifamycins of formula

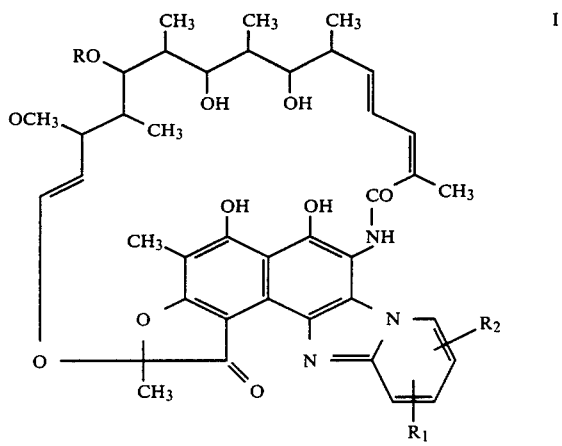

wherein R is hydrogen or acetyl, $R_1$ and $R_2$ independently represent hydrogen, $(C_{1-4})$-alkyl, benzyloxy, mono- or di-$(C_{1-3})$-alkylamino-$(C_{1-4})$-alkyl, $(C_{1-3})$-alkoxy-$(C_{1-4})$-alkyl, hydroxymethyl, hydroxy-$(C_{2-4})$-alkyl, cyano, halogen, nitro, mercapto, $(C_{1-4})$-alkylthio, phenylthio, carbamoyl, mono- or di-$(C_{1-4})$-alkyl-carbamoyl, or $R_1$ and $R_2$ taken together with two consecutive carbon atoms of the pyridine nucleus form a benzene ring optionally substituted by one or two methyl or ethyl groups.

The process comprises reacting the rifamycin O of formula

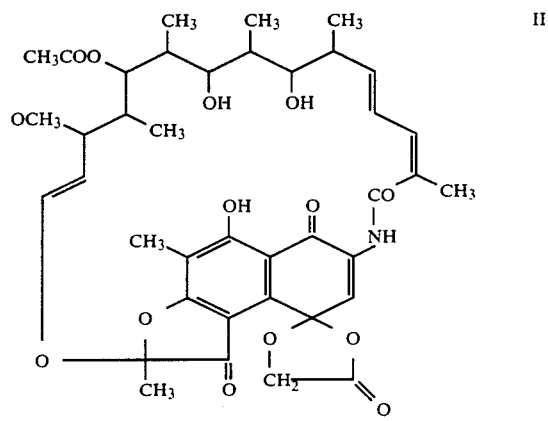

with a 2-aminopyridine of formula

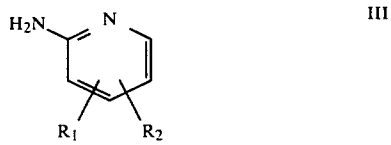

wherein $R_1$ and $R_2$ have the same meanings as before.

4 Claims, No Drawings

PROCESS FOR THE SYNTHESIS OF PYRIDO-IMIDAZO RIFAMYCINS

BACKGROUND OF THE INVENTION

Some of the compounds of formula I, more exactly those wherein R is hydrogen or acetyl and $R_1$ and $R_2$ independently represent hydrogen, $(C_{1-4})$-alkyl, benzyloxy, mono- or di-$(C_{1-3})$-alkylamino-$(C_{1-4})$-alkyl, $(C_{1-3})$-alkoxy-$(C_{1-4})$-alkyl, hydroxymethyl, hydroxy-$(C_{2-4})$-alkyl, nitro, or $R_1$ and $R_2$ taken together with two consecutive carbon atoms of the pyridine nucleus form a benzene ring optionally substituted by one or two methyl or ethyl groups are known in the patent literature; see, for instance, U.S. Pat. No. 4,341,785 published on July 27, 1982.

Other compounds of formula I, more exactly those wherein R is hydrogen or acetyl and at least one of $R_1$ or $R_2$ represents halogen, cyano, mercapto, $(C_{1-4})$-alkylthio, phenylthio, carbamoyl, mono- or di-$(C_{1-4})$-alkylcarbamoyl are described in the copending Italian patent application No. 3626 A/82, now available to the public.

In these two references a process for obtaining the compounds of formula I was also described.

Briefly, the known process was carried out by reacting a molar amount of a 3-halogen rifamycin S of formula

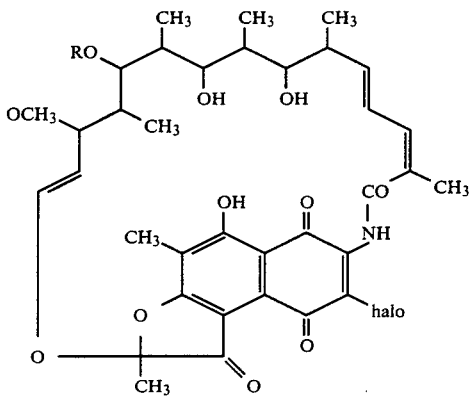

wherein R represented hydrogen or acetyl and halo preferably represented bromine or iodine, with from about 2 to about 8 molar equivalents of an appropriate 2-amino-pyridine of formula III.

A compound of formula

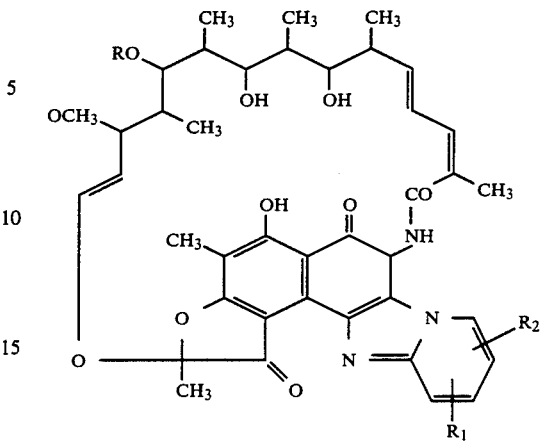

was obtained, which was preferably isolated and characterized, and was subsequently treated with ascorbic acid in order to give the end compounds of formula I.

Notwithstanding the yields of the two cited steps, calculated on the starting compound IV, are sometimes quite good (they are comprised between about 45% and about 75%), the process described in the U.S. patent is strongly limited by the fact that the starting compound IV is not a commercial product, but has to be prepared every time starting from rifamycin S with suitable, often troublesome, processes of halogenation. This fact causes the process described either in U.S. Pat. No. 4,341,785 and in the copending Italian application 3626 A/82 to run with yields far lower than those above mentioned, thus giving the desired compounds with unsatisfactory yields from an industrial point of view.

SUMMARY OF THE INVENTION

The present invention refers to a new method for preparing pyrido-imidazo-rifamycins of general formula

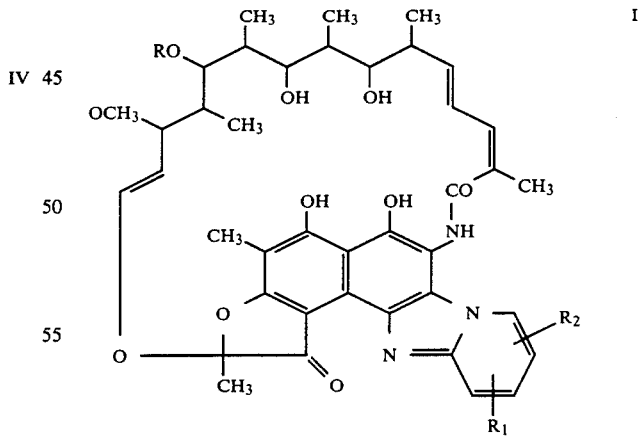

wherein R is hydrogen or acetyl, $R_1$ and $R_2$ independently represent hydrogen, $(C_{1-4})$-alkyl, benzyloxy, mono- or di-$(C_{1-3})$-alkylamino-$(C_{1-4})$-alkyl, $(C_{1-3})$-alkoxy-$(C_{1-4})$-alkyl, hydroxymethyl, hydroxy-$(C_{2-4})$-alkyl, cyano, halogen, nitro, mercapto, $(C_{1-4})$-alkylthio, phenylthio, carbamoyl, mono- and di-$(C_{1-4})$-alkyl-carbamoyl, or $R_1$ and $R_2$ taken together with two consecutive carbon atoms of the pyridine nucleus form a benzene ring optionally substituted by one or two methyl or ethyl groups.

In the context of the invention, the term $(C_{1-4})$-alkyl indicates straight or branched alkyl groups as, for instance, methyl, ethyl, propyl, isopropyl, butyl, sec.-butyl, isobutyl and tert.-butyl, while the term $(C_{1-3})$-alkoxy mainly designates the groups methoxy, ethoxy, propoxy or isopropoxy.

The compounds of formula I are endowed with outstanding antibacterial properties both in vitro and in vivo. Because of their poor absorption by animal organs and tissues when administered by oral route, they have proved to be particularly useful in combatting the microbial infections of the gastro-intestinal tract.

The process described in the present invention represents a remarkable improvement in comparison with the prior art method. In fact rifamycin O, which is a commercial product, is used as the starting rifamycin substrate [easily obtainable by chemical transformation of rifamycin B, as described in French Patent FM 739, or directly obtainable by fermentation of Nocardia strains (unexamined Japanese publication No. 15518/66) or by fermentation of Streptomyces strains (Belgian patent No. 751182)].

The rifamycin O is reacted under mild conditions with a selected 2-aminopyridine of formula III, in a suitable solvent or solvent system from which, by means of techniques known to a man skilled in the art, the desired end products are recovered, wherein $R_1$ and $R_2$ have the above mentioned meanings and R is acetyl, with yields varying from about 60% to about 90% calculated on the starting rifamycin O. The compounds of formula I so obtained can subsequently be subjected to an alkaline hydrolysis to give the corresponding compounds of formula I wherein R is hydrogen.

The reaction between the compounds of formula II and III therefore runs in only one step and is illustrated by the following scheme which does not report the optional hydrolytic step $R=COCH_3 \rightarrow R=H$.

SCHEME I

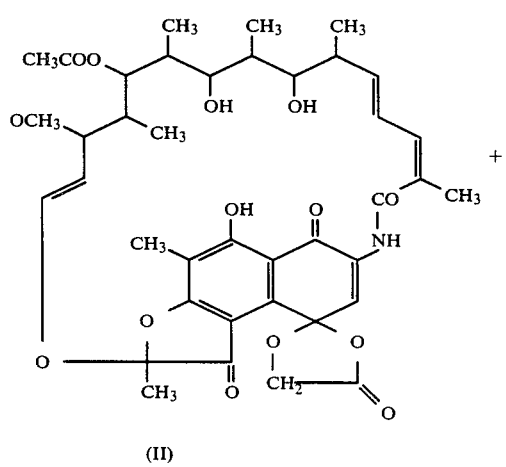

(II)

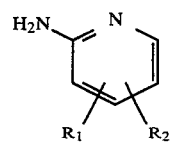

(III)

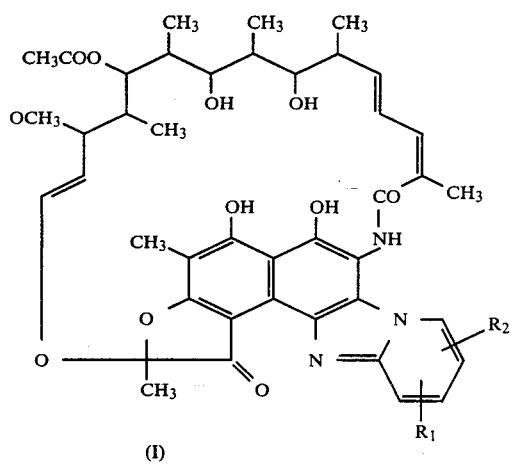

(I)

In practice, a molar amount of rifamycin O of formula II, is reacted with from about 1 to about 9 molar equivalents of a 2-aminopyridine of formula III and, preferably, from about 2 to about 6 molar equivalents of said aminopyridine.

The reaction is carried out in the presence of a solvent or of a solvent system, which is generally selected among those commonly used in rifamycins chemistry. For instance, aromatic hydrocarbons, like benzene and toluene, lower halogenated hydrocarbons, like methylene chloride, chloroform, 1,2-dichloroethane and analogs, lower alkanols, like methanol, ethanol, propanol, isopropanol or n-butanol, are advantageously used. Lower alkyl esters of lower aliphatic acids, glycols, acetonitrile, dioxane and tetrahydrofuran can also conveniently be employed. These solvents can be used alone, or in admixture among them, or also in admixture with water, in different volumetric ratios. The solvents which have given the best results are benzene, toluene, the lower halogenated hydrocarbons, the lower alkanols alone or in admixture with water, acetonitrile, glycols, dioxane and tetrahydrofuran.

The reaction takes place at ambient pressure and within wide limits of temperature, for instance between the room temperature and the boiling temperature of the reaction mixture. Usually, an interval comprised between the room temperature and about 60° C. gives absolutely satisfactory results.

The reaction is completed in a period of time which essentially depends on the nature of the aminopyridine substrate of formula III and on the conditions in which the reaction is carried out. Generally, from about 10 to about 100 hours are required to obtain the end products of formula I with the desired yields. It has been found, however, that, sometimes, the reaction course can be favored if the reaction itself is carried out in presence of iodine or of an appropriate system iodide/oxidizing agent, wherein the iodide can be, for instance, the iodide of an alkali or an alkaline-earth metal and the hydroiodide of the same starting 2-amino-piridine and the oxidizing agent can be an agent capable of oxidizing, in the employed reaction conditions, the iodide ion, in order to release iodine in the reaction ambient. The iodine, or the system iodide/oxidizing agent, can be present in the reaction ambient respectively in amounts from about 0.1 to about 1 molar equivalent, or in an amount which releases from about 0.1 to about 1 molar equivalent of iodine, for each mole of starting rifamycin O.

In such a case, however, the reaction solution must subsequently be treated with a suitable reducing agent, like, for instance, ascorbic acid, isoascorbic acid or dihydroxyacetone.

The above described operations are carried out without separating any intermediate, so preserving the "one step reaction" character typical of the process of the present invention.

The so obtained compounds of formula I in which R is the acetyl group are recovered from the reaction medium according to conventional techniques. Thus, for instance, the excess of unreacted aminopyridine of formula III is eliminated from the organic phase by means of an aqueous solution of a mineral acid. The organic phase is then separated and optionally dried on a suitable agent like, for instance, sodium sulfate, and the end product is obtained by evaporating the solvent. Alternatively, the desired compounds are obtained by crystallization from the reaction ambient at a temperature of about 0° to 10° C. when solvent systems containing water are used.

The compounds of formula I can be purified, if necessary, by crystallization from suitable solvents or solvent systems.

Subsequently, the products of formula I wherein R is acetyl can be transformed into the corresponding compounds wherein R is hydrogen by means of a mild alkaline hydrolysis. Alternatively, the same starting rifamycin O can be transformed into the corresponding desacetyl derivative on which the process of the invention can be carried out according to scheme I.

The invention is illustrated by means of the following examples which, however, have not to be interpreted as a limitation of the scope of the invention.

The I.R. spectra have been performed in KBr with a Perkin-Elmer 281-B spectrophotometer.

The $^1$H-NMR and $^{13}$C-NMR spectra have been performed in deuterochloroform with a Varian XL 100 spectrophotometer by using tetramethylsilane as internal standard. The U.V. spectra have been performed in absolute methanol with a Perkin-Elmer 552 spectrophotometer.

EXAMPLE 1

4-Deoxy-4'-methyl-pyrido[1',2':1,2]imidazo-[5,4-c]rifamycin SV 7.54 Grams (0.01 moles) of rifamycin O and 3.24 g (0.03 moles) of 2-amino-4-methyl-pyridine were dissolved in 40 ml of methylene chloride and the so obtained solution was kept at room temperature for 48 hours. After washing the reaction mixture first with 60 ml of an aqueous 1N solution of hydrochloric acid and then with water, and drying the organic phase over sodium sulfate, the methylene chloride was eliminated by evaporation under vacuum.

A residue was obtained which was crystallized by ethanol and water 7:3 (v/v). Yield 6.13 g (78% of theoretical). M.p. 200°–205° C. (decomposition).

| U.V. Spectrum: | λ max (mμ) | $E_{1cm}^{1\%}$ |
|---|---|---|
| | 232 | 489 |
| | 260 | 339 |
| | 292 | 295 |
| | 320 | 216 |
| | 370 | 119 |
| | 450 | 159 |

I.R. Spectrum: characteristic absorption bands were observed at the following frequencies (in cm$^{-1}$): 3440 (b), 2960 (s), 2920 (s), 2860 (w), 2820 (vw), 1705 (s), 1640 (s), 1580 (s), 1500 (s). b=broad, s=strong, w=weak, vw=very weak.

$^1$H-NMR Spectrum: characteristic resonance peaks were observed at the following δ (expressed as p.p.m.): −0.56 (d,3H); 0.14 (d,3H); 0.74 (d,3H); 0.94 (d,3H); 1.94 (s,3H); 1.98 (s,3H); 2.02 (s,3H); 2.26 (s,3H); 2.63 (s,3H); 3.00 (s,3H); 3.2–3.9 (m,3H); 4.15–5.20 (m,2H); 5.9–6.9 (m,4H); 7.06 (dd,1H); 7.38 (s,1H); 8.39 (s,1H); 8.43 (d,1H); 11.0 (s,1H); 13.12 (s,1H). s=singlet; d=doublet; m=multiplet; dd=doublet of doublet.

$^{13}$C-NMR Spectrum: characteristic resonance peaks were observed at the following δ (expressed as p.p.m.): 6.98; 8.06; 8.21; 10.76; 17.56; 20.43; 20.78; 21.44; 22.35; 32.91; 36.93; 37.78; 38.59; 56.99; 72.65; 73.91; 76.75; 77.86; 97.83; 103.86; 104.09; 108.97; 109.99; 112.03; 114.96; 115.52; 117.61; 119.26; 122.99; 125.35; 128.44; 128.96; 136.21; 138.87; 141.75; 142.10; 147.74; 155.10; 170.63; 171.89; 182.19; 188.84.

EXAMPLE 2

4-Deoxy-isoquinolino[2',1':1,2]imidazo[5,4-c]rifamycin SV

By substantially operating as described in the preceding example, starting from 7.54 g (0.01 moles) of rifamycin O and 4.32 g (0.03 moles) of 1-amino-isoquinoline, 6.07 g of the title compound were obtained (74% of theoretical). M.p. 181°–186° C. (decomposition).

| U.V. Spectrum: | λ max (mμ) | $E_{1cm}^{1\%}$ |
|---|---|---|
| | 253 | 532 |
| | 288 | 363 |
| | 300 | 346 |
| | 320 | 290 |
| | 382 | 120 |
| | 430 | 129 |

I.R. Spectrum: characteristic absorption bands were observed at the following frequencies (in cm$^{-1}$): 3440 (b), 3140 (b), 2910 (s), 2850 (w), 1700 (s), 1630 (b), 1610(b), 1580 (w), 1555 (vw), 1535 (vw) b=broad; s=strong; w=weak; vw=very weak.

$^1$H-NMR Spectrum: Characteristic resonance peaks were observed at the following δ (expressed as p.p.m.): −0.65 (d,3H); 0.04 (d,3H); 0.7 (d,3H); 0.88 (d,3H); 1.55 (s,3H); 1.92 (s,3H); 2.02 (s,3H); 2.27 (s,3H); 2.77 (d,1H); 2.94 (s,3H); 3.00–3.90 (m,4H); 4.78 (d,1H); 4.93 (q,1H); 5.75–7.00 (m,4H); 7.34 (d,1H); 7.6–8.0 (m,6H); 16.6 (m,1H). s=singlet, d=doublet; m=multiplet; q=quartet

EXAMPLE 3

3'-Bromo-4-deoxy-pyrido[1',2':1,2]imidazo[5,4-c]rifamycin SV

By operating as described in example 1, starting from 15.1 g (0.02 moles) of rifamycin O and 6.92 g (0.04 moles) of 2-amino-5-bromo-pyridine, 13.6 g (yield 80% of theoretical) were obtained.

| U.V. Spectrum: | λ max (mµ) | $E_{1cm}^{1\%}$ |
|---|---|---|
| | 225 | 481 |
| | 238 | 502 |
| | 298 | 345 |
| | 330 | 185 |
| | 378 | 107 |
| | 450 | 133 |

I.R. Spectrum: characteristic absorption bands were observed at the following frequencies (in $cm^{-1}$): 3440 (b); 3220 (w); 2960 (s); 2925 (m); 2870 (m); 1725 (w); 1715 (s); 1655 (w); 1635 (s); 1600 (vs). b=broad; m=medium; w=weak; s=strong; vs=very strong.

$^1$H-NMR Spectrum: characteristic resonance peaks were observed at the following δ (expressed as p.p.m.): −0.56 (d,3H); 0.13 (d,3H); 0.80 (d,3H); 0.85 (d,3H); 1.91 (s,3H); 1.94 (s,3H); 2.02 (s,3H); 2.26 (s,3H); 2.98 (s,3H); 2.60–3.00 (m,1H); 3.25 (d,1H); 3.56 (s,1H); 3.38–3.80 (m,2H); 4.84 (d,1H); 5.00 (q,1H); 6.02 (d,1H); 6.00–7.00 (m,3H); 7.60 (d,1H); 7.87 (q,1H); 8.39 (s,1H); 8.56 (d,1H); 16.80 (s,1H) s=singlet; d=doublet; q=quartet; m=multiplet.

$^{13}$C-NMR Spectrum: characteristic resonance peaks were observed at the following δ (expressed as p.p.m.): 7.13; 8.17; 10.86; 17.47; 20.41; 20.73; 21.28; 33.07; 37.12; 38.08; 38.77; 57.01; 72.94; 73.92; 76.80; 77.88; 98.48; 103.82; 105.11; 108.96; 109.28; 112.59; 112.81; 115.57; 116.33; 120.94; 123.38; 125.22; 129.06; 136.03; 136.80; 137.46; 141.96; 170.92; 171.59; 171.81; 182.62; 187.68.

EXAMPLE 4

4-Deoxy-4'-methyl-pyrido[1',2':1,2]imidazo[5,4-c]rifamycin SV

A solution of 3.47 g (0.0046 moles) of rifamycin O, 1.49 g (0.0138 moles) of 2-amino-4-methyl-pyridine and 0.28 g (0.0011 moles) of iodine in 20 ml of methylene chloride was kept at room temperature for 24 hours. After adding 2 ml of an aqueous 20% solution of ascorbic acid and stirring for 30 minutes, the reaction mixture was first washed with 40 ml of an aqueous 1N solution of hydrochloric acid and then with water to neutrality.

The organic phase was recovered, dried over sodium sulfate and evaporated under vacuum to obtain a residue which was crystallized by ethanol/water 7/3 (v/v). Yield 3.15 g (87% of theoretical).

The so obtained compound has the same chemico-physical characteristics as that obtained in Example 1.

EXAMPLE 5

4-Deoxy-3'-methyl-pyrido[1',2':1,2]imidazo[5,4-c]rifamycin SV

The compound was prepared according to the procedure described in example 2, starting from 15.1 g (0.02 moles) of rifamycin O and 6.48 g (0.06 moles) of 2-amino-5-methyl-pyridine. Yield 12.6 g (80% of theoretical). M.p. 193°–198° C. (decomposition).

| U.V. Spectrum: | λ max (mµ) | $E_{1cm}^{1\%}$ |
|---|---|---|
| | 218 | 493 |
| | 244 | 433 |
| | 258 | 338 |
| | 274 | 301 |
| | 294 | 315 |
| | 304 | 207 |
| | 360 | 104 |
| | 373 | 123 |
| | 448 | 166 |

I.R. Spectrum: characteristic absorption bands were observed at the following frequencies (in $cm^{-1}$): 3340 (b), 3300 (b), 2960 (s), 2925 (s), 2870 (vw), 2850 (s), 1730 (s), 1710 (vw), 1650 (vw), 1640 (s), 1600 (vw), 1585 (s), 1565 (w), 1525 (vw), 1505 (s) b=broad; s=strong; w=weak; vw=very weak.

$^1$H-NMR Spectrum: characteristic resonance peaks were observed at the following δ (expressed as p.p.m.): −0.7 (d,3H); 0.05 (d,3H); 0.68 (d,3H); 0.87 (d,3H); 1.73 (s,3H); 1.92 (s,3H); 1.97 (s,3H); 2.23 (s,3H); 2.63 (s,3H); 2.92 (s,3H); 3.25–4.00 (m,5H); 4.6–5.10 (m,2H); 5.9–6.8 (m,4H); 7.13 (q,1H); 7.6 (q,1H); 8.48 (q,1H); 14.14 (s,1H); 16.65 (s,1H) s=singlet; d=doublet; m=multiplet; q=quartet

EXAMPLE 6

4-Deoxy-4'-methyl-pyrido[1',2':1,2]imidazo[5,4-c]rifamycin SV 3.47 Grams (0.0046 moles) of rifamycin O, 1.49 g (0.0138 moles) of 2-amino-4-methyl-pyridine and 0.28 g (0.0011 moles) of iodine were dissolved in 15 ml of a 7/3 (v/v) mixture of ethanol/water. The resulting solution was stirred for 18 hours at room temperature, then 0.28 g of iodine were added and stirring was continued for further 2 hours. The reaction mixture was added with 0.53 g (0.003 moles) of ascorbic acid and left standing for 2 days at a temperature of about 5° C. The end product crystallized which, after filtration and drying, weighted 2.35 g (65% of theoretical). The compound has the same chemico-physical characteristics as that obtained in Example 1.

EXAMPLE 7

4-Deoxy-4'-methyl-pyrido[1',2':1,2]imidazo[5,4-c]rifamycin SV

200 Grams (0.265 moles) of rifamycin O and 65.5 g (0.607 moles) of 2-amino-4-methyl-pyridine were dissolved in 1000 ml of methylene chloride and were kept at room temperature for 40 hours. The reaction mixture was washed with 900 ml of an aqueous 1N solution of hydrochloric acid and then with water to neutrality. The washing liquors were cast off, the organic layer was dried over sodium sulfate and, after evaporating the solvent under vacuum, a residue was obtained which was crystallized from a 7/3 (v/v) mixture of ethanol/water. Yield 177 g (85% of theoretical). The compound has the same chemico-physical characteristics as that obtained in Example 1.

EXAMPLE 8

4-Deoxy-4'-methyl-pyrido[1',2':1,2]imidazo[5,4-c]rifamycin SV

The procedure of example 7 is repeated, keeping the reaction solution at room temperature for 20 hours and in presence of 11 g (0.043 moles) of iodine. After treatment with 130 ml of aqueous 20% solution of ascorbic acid, 160.4 g (77% of theoretical) of title compound were obtained, identical with that obtained in Example 1.

EXAMPLE 9

4-Deoxy-4'-methyl-pyrido-[1',2':1,2]imidazo[5,4-c]rifamycin SV

100 Grams (0.132 moles) of rifamycin O and 57.1 g (0.528 moles) of 2-amino-4-methyl-pyridine were stirred in 400 ml of a 1:1 (v/v) mixture of ethanol/water at room temperature for 20 hours. The obtained solid was washed with a 1:1 (v/v) mixture of ethanol/water and then dried under vacuum, thus obtaining 86 g of pure product having the same chemico-physical characteristics as that obtained in Example 1, with a yield of 82% of theoretical.

EXAMPLE 10

4-Deoxy-4'-methyl-pyrido-[1',2':1,2]imidazo[5,4-c]rifamycin SV

By substantially operating according to Example 9, employing a smaller quantity of 2-amino-4-methyl-pyridine, ie. 42.8 g (0.396 moles), 83.5 g of pure title product were obtained with a yield of 79.5% of theoretical.

EXAMPLE 11

4-Deoxy-4'-methyl-pyrido-[1',2':1,2]imidazo[5,4-c]rifamycin SV

By employing the same molar ratio rifamycin O/2-amino-4-methyl-pyridine as in Example 10, using 450 ml of a 10:13 (v/v) mixture of ethanol/water and working under the same reaction conditions of Example 9, 91 g of pure title product were obtained with a yield of 86.7% of theoretical.

EXAMPLE 12

4-Deoxy-4'-methyl-pyrido-[1',2':1,2]imidazo[5,4-c]rifamycin SV 6.0 Grams (0.008 moles) of rifamycin O and 3.24 g of 2-amino-4-methyl-pyridine were stirred in 12 ml of a 9:1 (v/v) mixture of propylene glycol/ethanol for 18 hours at room temperature and the obtained mixture was left standing for 72 hours. After diluting with 16 ml of a 1:1 (v/v) mixture of 2N aqueous hydrochloric acid/ethanol the reaction mixture was filtered, the solid was collected, washed with a 1:1 (v/v) mixture of ethanol/water and dried to give 4.2 g of pure title product with a yield of 67% of theoretical.

EXAMPLE 13

4-Deoxy-4'-methyl-pyrido-[1',2':1,2]imidazo-[5,4-c]rifamycin SV

10 Grams (0.013 moles) of rifamycin O and 4.3 g (0.039 moles) of 2-amino-4-methyl-pyridine were stirred in 30 ml of a 3:2 (v:v) mixture of isopropanol/water for 16 hours at room temperature. The reaction mixture was subsequently filtered, the solid was washed with the same mixture of solvents used in the reaction and dried under vacuum to give 8.7 g of pure title product with a yield of 83% of theoretical.

EXAMPLE 14

4-Deoxy-4'-methyl-pyrido-[1',2':1,2]imidazo[5,4-c]rifamycin SV

By substantially operating according to Example 13, and employing tert.-butanol instead of isopropanol, 7.2 g of pure title product were obtained with a yield of 69% of theoretical.

The following compounds of formula I were prepared according to the procedures described in the foregoing Examples.

| R | $R_1$ | $R_2$ |
|---|---|---|
| $COCH_3$ | H | -4'-$CH_2OH$ |
| $COCH_3$ | H | -4'-$CH_2$—$CH_2$—$N(CH_3)_2$ |
| $COCH_3$ | H | -4'-$CH_2$—$N(CH_3)_2$ |
| $COCH_3$ | H | -4'-$OCH_2C_6H_5$ |
| $COCH_3$ | H | -4'-$NO_2$ |
| $COCH_3$ | -3-$CH_3$ | -4'-$CH_2$—$CH_2$—$CG_2$—$N(CH_3)$ |
| $COCH_3$ | -5'-$CH_3$ | -3'-$CH_2$—$CH_2$—$N(CH_3)_2$ |
| $COCH_3$ | H | -3'-SH |
| $COCH_3$ | -3'-Br | -5'-Br |
| $COCH_3$ | H | -3'-$CH_3$ |
| $COCH_3$ | H | -4'-CO—$NH_2$ |
| $COCH_3$ | H | -4'-CO—$N(CH_3)_2$ |
| $COCH_3$ | -3'-Br | -4'-$CH_2$—$N(CH_3)_2$ |
| $COCH_3$ | H | -4'-S—$C_6H_5$ |

We claim:
 1. A new process for the preparation of pyrido-imidazo rifamycins of formula

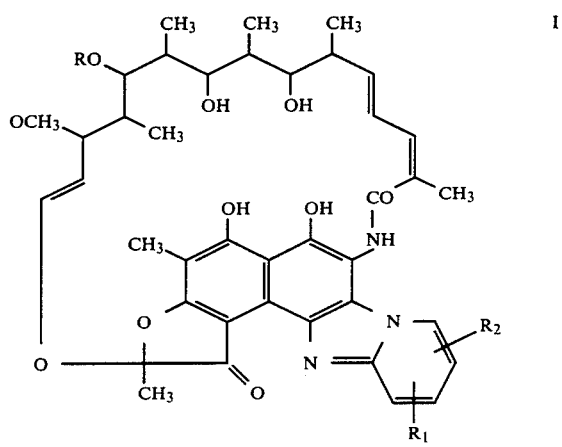

wherein R is hydrogen or acetyl, $R_1$ and $R_2$ independently represent hydrogen, ($C_{1-4}$)-alkyl, benzyloxy, mono- or di-($C_{1-3}$)-alkylamino-($C_{1-4}$)-alkyl, ($C_{1-3}$)-alkoxy-($C_{1-4}$)-alkyl, hydroxymethyl, hydroxy-($C_{2-4}$)-alkyl, cyano, halogen, nitro, mercapto, ($C_{1-4}$)-alkylthio, phenylthio, carbamoyl, mono- or di-($C_{1-4}$)-alkyl-carbamoyl, or $R_1$ and $R_2$ taken together with two consecutive carbon atoms of the pyridine nucleus, form a benzene ring optionally substituted by 1 or 2 methyl or ethyl groups, which comprises reacting a molar equivalent of rifamycin O of formula

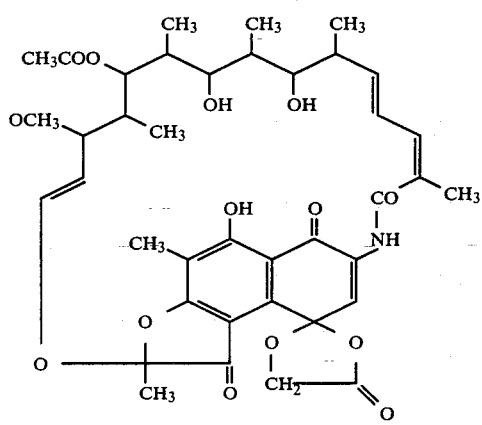

with from about 1 to about 9 molar equivalents of a 2-aminopyridine of formula

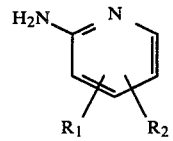

in the presence of a solvent or a solvent system, at a temperature comprised between about the room temperature and the boiling temperature of the reaction mixture, for a period of time comprised between about 10 and about 100 hours, optionally in presence of iodine or of a system iodide/oxidizing agent, and recovering the end products by means of known techniques.

2. A process as defined in claim 1, wherein for each molar equivalent of rifamycin O, from about 2 to about 6 molar equivalents of 2-aminopyridine of formula III are used.

3. A process as defined in claim 1, wherein the solvent or solvent system is selected among lower halogenated hydrocarbons, lower alkanols, lower alkyl esters of lower aliphatic acids, acetonitrile, glycols, dioxane, tetrahydrofuran alone or in admixture among them or in admixture with water in different volumetric ratios.

4. A process as defined in claim 1, wherein, for each molar equivalent of rifamycin O, from about 0.1 to about 1 molar equivalents of iodine or of a system iodide/oxidizing agent is used.

* * * * *